US006313090B1

(12) United States Patent
Rogers et al.

(10) Patent No.: US 6,313,090 B1
(45) Date of Patent: Nov. 6, 2001

(54) METHODS FOR TREATING PARASITIC INFECTION USING THIOPEPTIDES

(75) Inventors: Martin John Rogers, Newark, DE (US); Thomas F. McCutchan, Rockville, MD (US); Glenn A. McConkey, Ilkley (GB); Alexandra S. Fairfield, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/446,765

(22) PCT Filed: Jul. 7, 1997

(86) PCT No.: PCT/US97/11939

§ 371 Date: Mar. 20, 2000

§ 102(e) Date: Mar. 20, 2000

(87) PCT Pub. No.: WO99/02176

PCT Pub. Date: Jan. 21, 1999

(51) Int. Cl.[7] .................. A61K 31/427; A61K 31/43; A61K 38/04
(52) U.S. Cl. ..................... 514/2; 514/365; 514/368
(58) Field of Search ................... 514/2, 365, 368

(56) References Cited

FOREIGN PATENT DOCUMENTS 58-043922 * 3/1983 (JP) .

OTHER PUBLICATIONS

Rogers et al. "The Antibiotic Micrococcin is a Potent Inhibitor of Growth and Protein Synthesis in the Malaria Parasite" *Antimicrobial Agents and Chemotherapy* 42(3):715–716, Mar. 1998.

McConkey et al. "Inhibition of *Plasmodium falciparum* Protein Synthesis" *J. Biol. Chem.* 272(4):2046–2049, Jan. 24, 1997.

Rogers et al. "Interaction of Thiostrepton with an RNA Fragment Derived from the Plastid–Encoded Ribosomal RNA of the Malaria Parasite" *RNA* 3:815–820, 1997.

McFadden et al. "Plastid in Human Parasites" *Nature* 381:482, Jun. 6, 1996.

Clough et al., "Thiostrepton binds to malarial plastid rRNA," *Febs Letters*, 406:123–125 (1997).

* cited by examiner

*Primary Examiner*—Phyllis G. Spivack
(74) *Attorney, Agent, or Firm*—Needle & Rosenberg, P.C.

(57) ABSTRACT

The present invention provides a method for treating a parasitic infection in a subject infected with a parasite having a plastid-like organelle, comprising administering to the subject an infection treating amount of a thiopeptide in a pharmaceutically acceptable carrier. Methods for treating Cryptospordium, Toxoplasma or Plasmodium infection in a subject are also provided, each method comprising administering to the subject an infection treating amount of a thiopeptide in a pharmaceutically acceptable carrier.

24 Claims, 1 Drawing Sheet

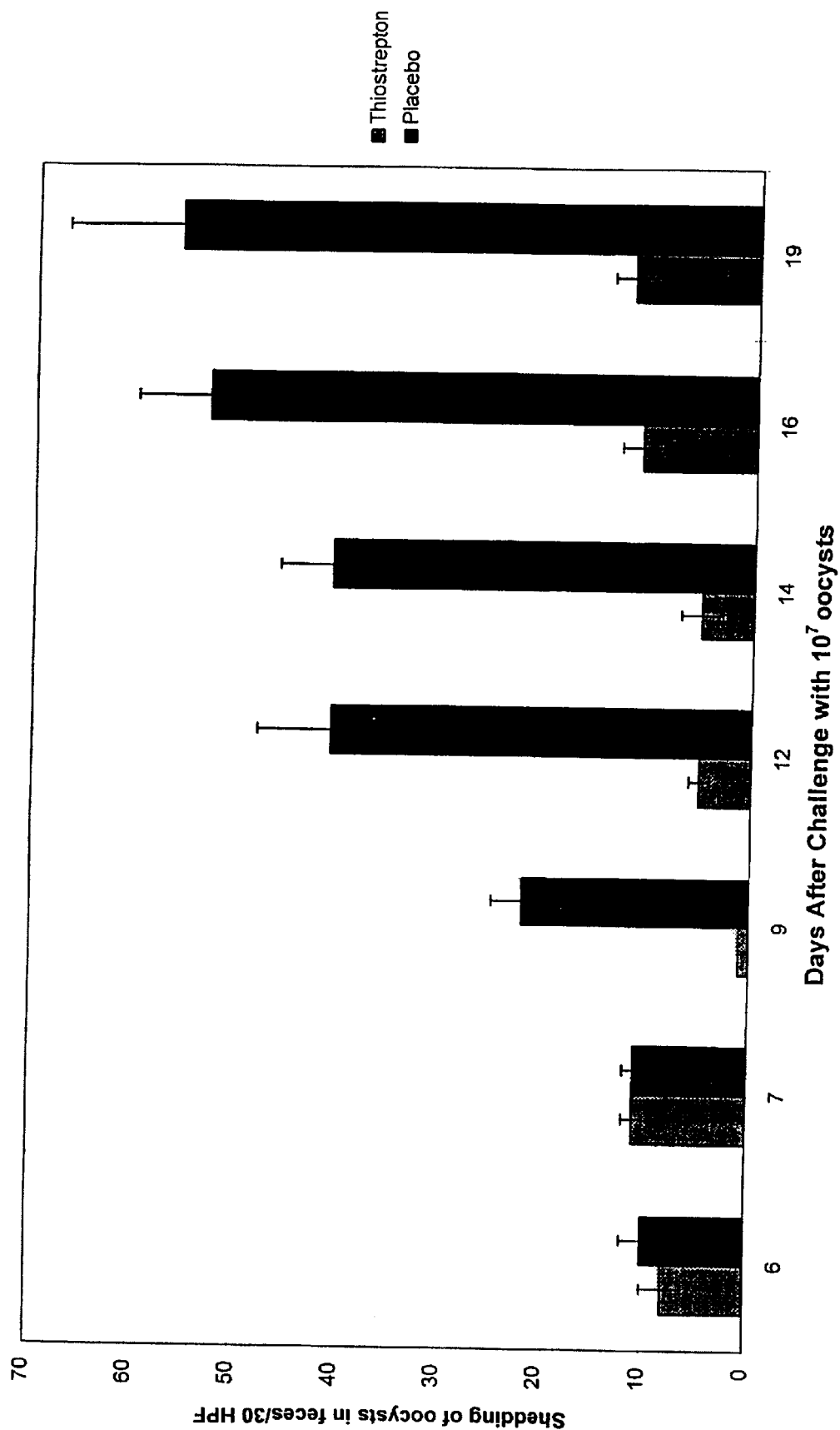

US 6,313,090 B1

METHODS FOR TREATING PARASITIC INFECTION USING THIOPEPTIDES

This application claims priority to and is a national phase application filed under 35 U.S.C. § 371 of International Application No. PCT/US97/11939, filed Jul. 7, 1997, which application is incorporated herein in its entirety by reference.

This invention was made with government support under the National Institutes of Health Intramural Research Program. The government has certain rights in this invention.

BACKGROUND ART

1. Field of the Invention

The present invention provides methods for treating parasitic infections in animals using thiopeptides. In particular, this invention relates to the treatment of parasitic infections caused by members of the phylum Apicomplexa (e.g., Cryptospordium, Plasmodium, Toxoplasma) by administering thiopeptides in a pharmaceutically acceptable carrier.

2. Background Art

Thiopeptides are sulfur-rich peptide antibiotics containing multiple thiazole rings which are naturally produced by streptomycetes (37). These antibiotics, of which thiostrepton is an example, inhibit translation and ribosomal GTPase activity by binding to a limited and conserved region in the large subunit (LSU) rRNA found in eubacteria and organelles and not the corresponding region in eucarya (12–14).

Plasmodium, the agent responsible for malaria, is an obligate intracellular parasite. More than ten years ago an urgent need for drugs against malaria was identified (33). The antibiotics currently in use, including the tetracyclines and clindamycin, for the treatment and prophylaxis of malaria have little action on pre-erythrocytic stages and a slow action on blood stages, but are used for treatment of drug resistant strains because of their safety rather than their efficacy (34,35). Furthermore, the rapid spread of resistance to chloroquine has heightened the need for ready availability of relatively low cost prophylactic and therapeutic anti-malarial drugs. These include compounds that reverse resistance to chloroquine, compounds that act rapidly to treat falciparum malaria and others that can be administered by methods other than injection (to avoid the use of contaminated needles).

Human clinical cryptosporidiosis infection varies with host immune competence from mild, self-limiting diarrhea to life-threatening enteritis complicated by extraintestinal disease. There is no reliable therapy for cryptosporidiosis. The problems of developing in vitro and in vivo methods of screening drugs, such as limited availability and poor reproducibility, have contributed to this lack of effective treatment. However, the major hindrance has been a lack of understanding of the parasite, its virulence and its interactions with the host's immune system (42).

The present invention overcomes previous shortcomings in developing effective treatments of these types of parasitic infections by providing a method for treating such infections in subjects caused by parasites having a plastid-like organelle by administering thiopeptides to the subject.

BRIEF DESCRIPTION OF THE DRAWINGS

FIG. 1 shows the amount of oocysts shed after administering thiostrepton (500 mg/kg/day) or placebo to scid mice preconditioned with monoclonal antibodies against interferon-γ and orally infected with $10^7$ Cryptospordium parvum oocysts.

SUMMARY OF THE INVENTION

The present invention provides a method for treating a parasitic infection in a subject infected with a parasite having a plastid-like organelle, comprising administering to the subject an infection treating amount of a thiopeptide in a pharmaceutically acceptable carrier.

Methods are also provided for treating Cryptospordium, Toxoplasma or Plasmodium infection in a subject, each method comprising administering to the subject an infection treating amount of a thiopeptide in a pharmaceutically acceptable carrier.

Various other objectives and advantages of the present invention will become apparent from the following description.

DETAILED DESCRIPTION OF THE INVENTION

As used in the claims, "a" can include one or more.

The present invention provides a method for treating a parasitic infection in a subject infected with a parasite having a plastid-like organelle, comprising administering to the subject an infection treating amount of a thiopeptide in a pharmaceutically acceptable carrier. The subject of the invention can be any animal which can become infected by a parasite having a plastid-like organelle. For example, the animal of this invention can be, but is not limited to, cows, sheep, goats, pigs, birds (e.g., ducks, geese, turkeys, chickens) and shellfish. In a preferred embodiment, the animal can be a mammal and most preferably is a human. As used herein, the term "plastid-like organelle" means a circular, extrachromosomal DNA of eubacterial origin residing in a membrane-bound organelle, sharing features such as ribosomal RNA (rRNA) and transfer RNA (tRNA) gene organization with the plastids found in Euglena, red algae and green algae. The plastid-like organelle is also known as an apiplast (Apicomplexan plastid).

The parasite of the present invention can be any parasite now known or later identified to have the plastid-like organelle of the present invention. For example, the parasite of the invention can be of, but is not limited to, the *Apicomplexa phylum* such as, for example, Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus and Gregarina spp.; *Pneumocystis carinii;* members of the *Microspora phylum* such as, for example, Nosema, Enterocytozoon, Encephalitozoon, Septata, Mrazelia, Amblyospora, Ameson, Glugea, Pleistophora and Micropo-ridium spp.; and members of the *Ascetospora phylum* such as, for example, Haplosporidium spp. (39), as well as any other parasite identified as having a plastid-like organelle of the present invention The thiopeptide of the invention can be any member of the class of compounds characterized as sulfur-rich peptide antibiotics with multiple thiazole rings (37) now known or later identified to inhibit protein synthesis in the plastid-like organelle of parasites. For example, the thiopeptide can be, but is not limited to, thiostrepton: Ile-Ala-Ser-Ala-Ser-Cys-Thr-Thr-DCys-Ile-Cys-Thr-Cys-Ser-Cys-Ser-Ser-Ser (SEQ ID NO:8) (also known as A-8506, antibiotic 6761–31, antibiotic A 8506, antibiotic X 146, bryamycin, thiactin and X 146), micrococcin P, hosiheptide (also known as multhiomycin), siomycin, sporangiomycin, althiomycin, the thiociffins and/or thiopeptin, as well as any other sulfur-rich peptide antibiotic containing multiple thiazolerings, produced by streptomycetes or other peptide antibiotic-producing organisms.

To treat a parasitic infection caused by a parasite having a plastid-like organelle, the thiopeptide of the present invention can be administered to the subject orally, parenterally, intranasally (i.e., by aerosol) or topically. The thiopeptide can be in a pharmaceutically acceptable carrier. By "pharmaceutically acceptable" is meant a material that is not biologically or otherwise undesirable, i.e., the material may be administered to a subject, along with the thiopeptide without causing any undesirable biological effects or interacting in a deleterious manner with any of the other components of the pharmaceutical composition in which it is contained. The carrier would naturally be selected to minimize any degradation of the active ingredient and to mninimize any adverse side effects in the subject.

To treat a parasitic blood-stage infection (e.g., a malaria or babesia infection), parenteral administration can be the preferred mode. Suitable carriers for parenteral administration of the thiopeptide in a sterile solution or suspension can include sterile saline that may contain additives, such as ethyl oleate or isopropyl myristate, and can be injected, for example, intravenously, as well as into subcutaneous or intramuscular tissues.

Suitable carriers for oral administration include one or more substances which may also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pyrogen free saline, pharmaceutically accepted oils, or a mixture of any of these. The liquid can also contain other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel.

The thiopeptides of the present invention can be administered to the subject in amounts sufficient to treat the parasitic infection in the subject as desired. Optimal dosages used will vary according to the individual and the particular parasitic infection, on the basis of age, size, weight, condition, etc, as well as the particular treatment effect being induced. One skilled in the art will realize that dosages are best optimized by the practicing physician and methods for determining dosage are described, for example, in *Remington's Pharmaceutical Sciences* (36).

In a preferred embodiment, the thiopeptide of the present invention can be administered to a human or a non-human animal in a pharmaceutically acceptable carrier in a dosage range of about 50 to 550 mg/kg/day and is preferably administered in a dosage of about 500 mg/kg/day. Treatment can be continued for an indefinite period of time, as indicated by monitoring of the signs, symptoms and clinical parameters associated with the parasitic infection according to protocols standard in the art for monitoring parasitic infections. Examples of the parameters that would be monitored can include, but are not limited to, amount and frequency of diarrheal excretion, oocyst excretion, culture of the parasite in body fluids and tissues, body weight and blood chemistry and urine analysis of hepatobiliary function. Oocyst excretion can be measured by quantitation of acid-fast stained stool specimens, ELISA antigen capture, immunofluorescence assay, DNA amplification, etc., according to protocols well known in the art.

In a particular embodiment, the present invention provides a method for treating Cryptospordium infection in a subject, preferably human, comprising administering to the subject an infection treating amount of a thiopeptide in a pharmaceutically acceptable carrier. To treat a Cryptoporidium infection, the thiopeptide of this invention would preferably be administered to the subject orally.

In another embodiment, the present invention provides a method for treating Plasmodium infection in a subject, preferably human, comprising administering to the subject an infection treating amount of a thiopeptide in a pharmaceutically acceptable carrier. To treat a Plasmodium infection, the thiopeptide of this invention would preferably be administered to the subject parenterally.

A further embodiment of the present invention provides a method for treating Toxoplasma infection in a subject, preferably human, comprising administering to the subject an infection treating amount of a thiopeptide in a pharmaceutically acceptable carrier. To treat a Toxoplasma infection, the thiopeptide of this invention would preferably be administered to the subject parenterally.

It is also contemplated that the thiopeptide of the present invention can be administered in combination with other thiopeptides and/or other antibiotics, in particular, peptidyl transferase inhibitors (40) such as amicetin, anisomycin and chloraamphenicol to treat a parasitic infection in a subject. Thus, the present invention provides a composition comprising a thiopeptide and a peptidyl transferase inhibitor in a pharmaceutically acceptable carrier, such as a composition comprising thiostrepton and amicetin, thiostrepton and anisomycin, thiostrepton and chloramphenicol and the like.

Other antibiotics which can be combined with the thiopeptides of the claimed invention can include, but are not limited to, paromomycin, azithromycin, clarithromycin, nitazoxanide, novobiocin, fusidic acid, nalidixic acid, doxycycline, immune globulin preparations and several malarial compounds (e.g., mefloquine and halofantine and their analogs, pentanidine and its analogs) for treating Cryptospordium infection; pyrimethamine, sulfadiazine, atovaquine, fusidic acid and rifbutin for treating Toxoplasma infection; bactrim (trimethoprim/sulfa), atovaquone and pentamidine for treating Pneumocystis infection; and monensin, salinomycin, diclazuril, lasalocid, robenidine, nicarbazin, sinefungin and various ionophores for treating Eimeria infection. Thus, the present invention contemplates a composition comprising a thiopeptide and one or more antibiotics identified to be effective in treating parasitic infections, in a pharmaceutically acceptable carrier. This combination can be administered orally, parenterally, intranasally or topically as described above for thiopeptide administration and the same parameters regarding treatment and dosage as described above can be applied. Compositions comprising the above novel combinations are provided.

Also contemplated for the present invention is a composition comprising a thiopeptide (with or without other antibiotics) and an adjuvant to enhance the therapeutic or prophylactic effect of the thiopeptide. The adjuvant can be selected by standard criteria based on the particular thiopeptide used, the mode of administration and the subject (45). For example, the composition can include Freund's complete adjuvant, Freund's incomplete adjuvant, aluminum hydroxide or any other adjuvant known to enhance the therapeutic or prophylactic effect of the thiopeptide.

The present invention is more particularly described in the following examples which are intended as illustrative only since numerous modifications and variations wherein will be apparent to those skilled in the art.

EXAMPLES

I. Studies on Plasmodium

Assay of Growth inhibition. Thiostrepton (1525 u/mg; Calbiochem) and anisomycin (Sigma) were dissolved at 100 mM in DMSO (Pierce). *P. falciparum* (strain 3D7) (44) was maintained in culture with human erythrocytes (5% hematocrit) in RPMI-1640 (Life Technologies) supplemented with HEPES and sodium bicarbonate and human sera (10%) under standard conditions (18,19). The growth inhibition assay was conducted as described (20). Briefly, the parasitemia was adjusted to 0.1% parasitemia, 2.5% hematocrit and 200 µl aliquots placed in wells of a microtitre dish. Serial dilutions of drugs were made in RPMI. Thiostrepton was diluted to 10 mM in DMSO before the serial dilutions in RPMI. Aliquots (20 µl) were added in triplicate to the cultures in the microtitre plate, mixing well. At the highest concentrations (final 0.2mM), thiostrepton precipitates. After incubation for 48 hours under standard conditions, [2,8-$^3$H]-hypoxanthine Moravek Biochemicals, 12.5 Ci/mmol) in RPMI (20 µl, 0.05 mCi/ml) was added to each well. After incubation for a further 24 hours, the cultures were lysed and incorporated radioactivity was measured with an automated counter.

Assay of Inhibition of Protein Synthesis. Assay for inhibition of protein synthesis was similar to above except the culture and drug dilutions were in RPMI-1640 without leucine (Select-Amine, Life Technologies) and the sera was extensively dialyzed as described (21). Also, the cultures were adjusted to 1% parasitemia prior to the experiment. Microtitre plates were set up with drug dilutions as described above except cultures were incubated with drug for only 4 hours. [3,4,5-$^3$H]-Leucine (Moravek Biochemicals, 122 Ci/mmol, 0.5 mCi/ml, 100 µCi) was diluted to 4 ml in RPMI without leucine. The radiolabeled leucine (20 µl, 1 mCi) was added to each well and the plates were further incubated for four hours. The microtitre plates were processed as above to quantitate the incorporated radiolabel.

As of organelle and cyloplasmic transcript levels. RNA polymerase transcript levels were assessed by comparing the amounts of RNA synthesized at timepoints following drug treatment. Cultures of *P. falciparum* (3.2% parasitemia, 5% hematocrit) were treated with thiostrepton at 8 µM and rifampin (Sigma) at 80 µM; near the IC$_{99}$ values (this study and ref. 22). Aliquots (5 ml) of treated and control cultures were removed and immediately processed for RNA with a guanidinium thiocyanate solution, according to the manufacturer's directions (RNAgents, Promega). All RNA samples were dissolved in 50 µl DEPC-treated water, DNase I treated as previously described (23) and an aliquot (1 µl) was removed for RT-PCR First strand synthesis of cDNA was completed with a random hexamer (Superscript Preamplification System, Life Technologies). One-tenth of the CDNA product was utilized for PCR of rpoB/C, MSA1, and rRNA. Primers corresponding to the 3' region of rpoB, 5'-GGGCTTTAGAAGCTTTTGG-3' (SEQ ID NO:1), and the 5' region of rpoC, 5'-CCATTTAAAATTGGTAATCCTG-3' (SEQ ID NO:2) were applied as described (2,3) for PCR of nascent rpoB/C transcripts. Reactions were cycled with the following parameters: 94° C./30 seconds, 42° C./30 seconds, 72° C./60 seconds, 35 cycles. Primers for amplification of nucleotide 64 to 614 of MSA1 with 5'-GTGTGATAATATTCATGG-3' (SEQ ID NO:3) and 5'-GGAGAGCATTTGGTG-3' (SEQ ID NO:4)(24) and the small subunit rRNA with oligonucleotides 841 and 844 (23) were used for amplification reactions following the parameters in the respective references except with 35 cycles. Samples were also analyzed after 25 cycles of amplification to ensure detection in the linear range of the amplification reaction, with similar results. Following electrophoresis of aliquots from the amplification reactions on 1% agarose:TBE gels, samples were transferred to nylon membranes (GeneScreen Plus, DuPont) and hybridized as described (25). The amplification products were probed with 5'-$^{32}$P-labeled oligonucleotides. The rpoB/C products were probed with 5'-GTTTAGCTATTAATATAGAAGC-3' (SEQ ID NO:5) (nucleotide 2009–2030 of rpoB) and 5'-CGGAGAGGTATTAATACC-3' (SEQ ED NO:6) (nucleotide 108–125 of rpoC), in 5×SSC, 10 mM sodium phosphate, 0.05% sodium pyrophosphate, 1% sodium dodecyl sulfate, 5×Denhardt's solution, 100 µg/ml yeast tRNA, 42° C. and washed in the hybridization solution lacking Denhardt's and tRNA at 37° C., three times. The final wash was 1×SSC, 0.5% sodium dodecyl sulfate, 42° C. followed by autoradiography. The same results were obtained with either probe. The MSA1 amplification products were similarly probed with 5'-AAACTTGTGTTCGGATATAG-3' (SEQ ID NO:7) and the rRNA products with oligonucleotide 842 (23).

Assay of inhibition. The effect of thiostrepton on growth and protein synthesis of *P. falciparum* was compared to anisomycin, since the effect of both of these drugs is on protein synthesis. To assay the effect of thiostrepton and anisomycin on the growth of *P. faciparum*, inhibition of the uptake and incorporation of [$^3$H]hypoxanthine was quantitated at serial dilutions of the drugs on an in vitro culture of *P. falciparum*. Both compounds inhibited growth in the micromolar range (IC$_{50}$, 1.8 µM for thiostrepton and 0.5 µM for anisomycin). These values are comparable to previously published data for anisomycin (28). Inhibition of the incorporation of [$^3$H]leucine was also tested at the same dilutions of the drugs. For anisomycin, total protein synthesis was inhibited 50% at the IC$_{50}$ (0.511 µM) for inhibition of growth, with the concentration-response almost superimposable on that of protein synthesis. However, for thiostrepton, only a negligible amount of inhibition of total protein synthesis was observed at the IC$_{50}$ for growth. More than ten-fold higher concentrations than the IC$_{50}$ of thiostrepton were required for almost complete inhibition of total protein synthesis. The lack of inhibition of protein synthesis with thiostrepton at the IC$_{50}$ for inhibition of growth suggested that the principal target for the drug is different than cytoplasmic protein synthesis. This would occur if organelle protein synthesis was the target of inhibition (29,30).

The target of inhibition by thiostrepton. In the absence of a direct measure of plastid-like organelle protein synthesis, assay of mRNA levels by RT/PCR provides a sensitive assay for the selective effect of thiostrepton on the plastid-like organelle. The presence of a protein encoded by the organelle, identified in the 35-kb genome as a homolog of eubacterial RNA polymerase encoded by the rpoB and rpoc genes (5), was assayed during treatment. Selective inhibition of the plastid-like RNA polymerase with rifampin provides a comparison with the effect of thiostrepton, since prokaryotic RNA polymerases are sensitive to rifampin. The synthesis of the rpoB/C mRNA encoded by the 35-kb genome was then compared to a nuclear-encoded mRNA On the basis that the 35-kb encoded rpoB and rpoC are transcribed as a polycistronic mRNA (3), nascent transcripts were assayed at various timepoints during drug treatment by RT/PCR of the mRNA including the intergenic spacer between rpoB/C. Also, the sensitivity of RT/PCR provides a relative estimate of the mRNAs corresponding to those encoded on the 35-kb genome versus those of nuclear-encoded mRNAs. Amplification of part of the mRNA corresponding with Merozoite Surface Antigen (MSA1) was chosen as a nuclear-encoded mRNA, as this is abundant in erythrocytic stages of *P. falciparum* (24). As a control, a section of nuclear-encoded SSU rRNA was also amplified as this is unaffected by antibiotics.

The results show that thiostrepton and rifampin have similar effects on the decay of mRNA corresponding to rpoB/C; occurring within 6 hours of drug treatment. A time course with thiostrepton showed a decline of the rpoB/C product with time, with a notable affect after only one hour of treatment. Within the duration of the experiment (8 hours), the level of rpoB/C in untreated controls was consistent. Although thiostrepton may be inhibiting a specific subset of nuclear-encoded mRNAs, as the plastid RNA polymerase is composed of subunits of both nuclear and organelle origin, there was no effect on the levels of nuclear-encoded MSA mRNA nor total rRNA Since completion of the erythrocytic cycle for *P. falciparum* takes about 48 hours, it would expected that the effect on nuclear-encoded mRNAs would be observed only with longer time points and would reflect cell death rather than specific targeting the plastid-like organelle. These data also indicated that rifampin is a specific inhibitor of the RNA polymerase encoded by the plastid-like organelle (31,32). The data presented here demonstrate that the target for thiostrepton is the LSU encoded by the 35-kb organelle, while the target for anisomycin is the nuclear-encoded LSU rRNA and perhaps organelle-encoded LSU rRNAs. Although the function of the 35-kb plastid-like organelle is not known (5), inhibition of growth by thiostrepton indicates that protein synthesis from this organelle is essential for growth of the blood-stages of the parasite.

II. Studies on Cryposporidium

A. Experiment 1.

In vitro doses of drugs. Thiostrepton (Calbiochem) was dissolved in sterile complete Dulbecco's Modified Eagle Medium (DMEM) supplemented with dimethyl sulfoxide (DMSO) at 0.2% and tested at concentrations of 800, 400, 200, and 100, 10, 1 and 0.1 μg/ml.

Toxicity Testing Assay. 200 μl of medium containing drug at the above-mentioned concentrations and positive control preparations [paromomycin/DMSO (2 mg/ml/0.2%)] were introduced into two wells of a 96 well plate containing confluent MDBKF5D2 cell monolayers (ATCC accession number CCL-22) infected with intact *C. parvum* GCH1 oocysts (5.0×10⁴ per well) (43) and two wells without monolayers. The drug was incubated on the monolayers at 37° C. and 8% $CO_2$. At 48 hours, MTS (Owen's solution) and PMS were added to each well at concentrations of 333 μg/ml and 25 μM respectively. The plate was returned to the incubator in the dark to develop for two hours. At two hours, 100 μl of each supernatant was transferred to a new microtiter plate and the optical density (OD) was read in an ELISA plate reader at 490 nm.

Percent toxicity was calculated by subtracting the mean drug OD from the medium OD, divided by the medium OD, all of which was then multiplied by 100, as shown in the equation below. Cytotoxicity scores were assigned as follows: 0–5% toxicity=0, 6–25% toxicity=1, 26–50% toxicity=2, 51–75% toxicity=3, and 76–100% toxicity=4. As a standard, cytotoxicity scores of 0 or 1 were considered acceptable levels of toxicity. Toxicity scores of 2, 3, or 4 were considered as high levels of toxicity to the cell monolayer.

$$\frac{\text{OD medium} - \text{OD drug}}{\text{OD medium}} \times 100$$

Intact *C. parvum* oocyst asset 3.0×10⁴ *C. parvum* GCH1 oocysts per well were incubated in the above-mentioned concentrations of drug at 37° C. (8% $CO_2$) on confluent MDBKF5D2 cell monolayers in 96 well microtiter plates. The level of infection in each well was determined and analyzed by immunofluorescence assay at 48 hours, using *C. parvum* sporozoite rabbit anti-serum (0.1%) and fluorescein-conjugated goat anti-rabbit antibody (1.0%). Percent inhibition was calculated by subtracting the mean parasite/drug from the mean parasitelmedium, divided by the mean parasite/medium, all of which was multiplied by 100. The analysis was performed using MCID and an inverted microscope.

Tables 1 and 2 represent the results of two separate experiments. Medium and oocyst lysate toxicity levels are included. Thiostrepton appears to show good activity at concentrations of 200 and above with little toxicity to cells.

Experiment 2

In vitro doses of drugs. Thiostrepton (Calbiochem) and Phavic (NTZ) were dissolved in sterile complete Dulbecco's Modified Eagle Medium (DMEM) supplemented with dimethyl sulfoxide (DMSO) at 0.2% and tested at concentrations of 800, 400, 200, and 100 μg/ml. NTZ was tested at concentrations of 100, 10, 1 and 0.1 μg/ml. Paromomycin (Sigma) was dissolved in DMEM and tested at concentrations of 2000, 1000, 500 and 250 μg/ml.

Toxicity Testing Assay. 200 μl of medium containing drugs at the above-mentioned concentrations and positive control preparations [paromomycin/DMSO (2 mg/ml/0.2%)] were introduced into two wells of a 96 well plate containing confluent MDBKF5D2 cell monolayers infected with intact *C. parvum GCH*1 oocysts (5.0×10⁴ per well) and two wells without monolayers. The drug was incubated on the monolayers at 37° C. and 8% $CO_2$. At 48 hours, MTS (Owen's solution) and PMS were added to each well at concentrations of 333 μg/ml and 25μM respectively. The plate was returned to the incubator in the dark to develop for two hours. At two hours, 100 μl of each supernatant was transferred to a new microtiter plate and the optical density (OD) was read in an ELISA plate reader at 490 nm.

Percent toxicity was calculated by subtracting the mean drug OD from the medium OD, divided by the medium OD, all of which was then multiplied by 100, as shown in the equation below. Cytotoxicity scores were assigned as follows: 0–5% toxicity=0, 6–25% toxicity=1, 26–50% toxicity=2, 51–75% toxicity=3, and 76–100% toxicity=4. As a standard, cytotoxicity scores of 0 or 1 were considered acceptable levels of toxicity. Toxicity scores of 2, 3, or 4 were considered as high levels of toxicity to the cell monolayer.

$$\frac{\text{OD medium} - \text{OD drug}}{\text{OD medium}} \times 100$$

Intact *C. parvum* oocyst assay . 3.0×10⁴ *C. parvum* GCH1 oocysts per well were incubated in the above-mentioned concentrations of drug at 37° C. (8% $CO_2$) on confluent MDBKF5D2 cell monolayers in 96 well microtiter plates. For some monolayers, the oocysts were incubated in DMEM on the cell monolayers for four hours, at which time the monolayers were washed and then drug was added to the wells. The level of infection in each well was determined and analyzed by immunofluorescence assay at 48 hours, using C. parvum sporozoite rabbit anti-serum (0.1%) and fluorescein-conjugated goat anti-rabbit antibody (1.0%). Percent inhibition was calculated by subtracting the mean parasite/drug from the mean parasite/medium, divided by the mean parasite/medium, all of which was multiplied by 100. The analysis was performed using MCID and an inverted microscope.

Tables 3 and 4 show the results of washed versus unwashed monolayers, respectively. These data demonstrate that washing of cell monolayers four hours after infection did not alter outcome and that thiostrepton appears to be consistently effective in all assays compared with PRM. A consistent cytotoxicity of infected medium and medium with oocyst lysate is also indicated.

Experiment 3

In vitro doses of drugs. Thiostrepton (Calbiochem), Phavic (NTZ) were dissolved in sterile complete Dulbecco's Modified Eagle Medium (DMEM) supplemented with dimethyl sulfoxide (DMSO) at 0.2%. Thiostrepton was tested at a concentration of 800 μg/ml. NTZ was tested at a concentration of 10 μg/ml. Paromomycin was dissolved in DMEM and tested at 2000 μg/ml. Cell monolayers were infected and washed, followed by the addition of drug at time intervals of 0, 2, 4, 8 and 24 hours.

Toxicity Testing Assay. 200 μl of medium containing drug at the above-mentioned concentrations and positive control preparations [paromomycin/DMSO (2 mg/ml/0.2%)] were introduced into two wells of a 96 well plate containing confluent MDBKF5D2 cell monolayers infected with intact C. parvum GCH1 oocysts ($5.0 \times 10^4$ per well) and two wells without monolayers. The drug was incubated on the monolayers at 37° C. and 8% $CO_2$. At 48 hours, MTS (Owen's solution) and PMS were added to each well at concentrations of 333 μg/ml and 25μM respectively. The plate was returned to the incubator in the dark to develop for two hours. At two hours, 100 μl of each supernatant was transferred to a new microtiter plate and the optical density (OD) was read in an ELISA plate reader at 490 nm.

Percent toxicity was calculated by subtracting the mean drug OD from the medium OD, divided by the medium OD, all of which was then multiplied by 100, as shown in the equation below. Cytotoxicity scores were assigned as follows: 0–5% toxicity=0, 6–25% toxicity=1, 26–50% toxicity=2, 51–75% toxicity=3, and 76–100% toxicity=4. As a standard, cytotoxicity scores of 0 or 1 were considered acceptable levels of toxicity. Toxicity scores of 2, 3, or 4 were considered as high levels of toxicity to the cell monolayer.

$$\frac{\text{OD medium} - \text{OD drug}}{\text{OD medium}} \times 100$$

Intact C. parvum oocyst assay. $3.0 \times 10^4$ C. parvum GCH1 oocysts per well were incubated in the above-mentioned concentrations of drug at 37° C. (8% $CO_2$) on confluent MDBKF5D2 cell monolayers in 96 well microtiter plates. The level of infection in each well was determined and analyze by immunofluorescence assay at 48 hours, using C. parvum sporozoite rabbit anti-serum (0.1%) and fluorescein-conjugated goat anti-rabbit antibody (1.0%). Percent inhibition was calculated by subtracting the mean parasite/drug from the mean parasite/medium, divided by the mean parasite/medium, all of which was multiplied by 100. The analysis was performed using MCID and an inverted microscope.

Data presented in Tables 5 and 6 demonstrate that PRM is well within the normal range and thiostrepton appears to be consistently effective. Washing of monolayers four hours after infection did not alter the outcome. Consistent cytotoxicity levels of the infected medium and medium with oocyst lysate were also noted. These data show that both thiostrepton and NTZ act on the intracellular forms of the parasite, in much the same way as does PRM. However, unlike PRM, whose activity drops when it is added 24 after infection, both thiostrepton and NTZ were still highly inhibitory even i24 hours after infection.

In summary, thiostrepton was compared to paromomycin (PRM; used clinically for treatment) and Phavic (NTZ), also under development for activity against Cryptospordium parvum. For in vitro testing, the compounds were added at the time of cell invasion, so both sporozoite and intracellular stages were exposed. The drugs were also tested at time points following invasion, when only intracellular stages are present. Briefly, unlike PRK, both thiostrepton and NTZ were highly inhibitory even 24 hours after infection. This is consistent with thiostrepton targeting the plastid-like organelle as there should be no stage-specificity. Thiostrepton has also been shown to be more effective than PRM at about one-fifth the dose, with little toxicity to cells.

In vivo Testing

SCID mice (Taconic Farms, Germantown, N.Y.), preconditioned with monoclonal antibodies to interferon as described (41), were given an acute infection of C. parvum ($10^7$ oocysts given orally). A total of five mice in two groups were used. One group received 500 mg/kg/day (in two doses of 250 mg/kg) of thiostrepton six days post-infection and the other group received a placebo. Treatment lasted ten days and oocyst shedding was measured by counting the number of oocysts in 30 fields under high power microscopy of acid-fast stained fecal smears and calculating the mean for each group as described (41). The results in FIG. 1 showed that thiostrepton significantly reduced oocyst shedding (shaded bars) compared to placebo (black bars). These data are summarized in Table 7. Mucosal scores describe the extent of mucosal infection detected in formalin-fixed sections of tissue samples from various gut sites (pyloric region of stomach, liver, gallbladder, mid-small intestine, terminal ileum, cecum and colon) taken during necropsy. Scoring was as follows: 0 (no infection) to 5 (maximal infection) and was expressed as the combined score of the number of gut sites examined.

III. Methods for Treating Parasitic Infections in Humans and Non-human Animals

Treatment of parasitic infection in humans and non-human animals. To treat a parasitic infection in a human or non-human animal diagnosed as having an infection by a parasite having a plastid-like organelle, approximately 500 mg/kg/day of thiostrepton can be administered as a single dose or in multiple doses to the infected individual, either orally or parenteraly in a pharmaceutically acceptable carrier. The daily administration can be continued for an indefinite period for as long as signs and symptoms of the parasitic infection persist. The signs and symptoms of the infected individual which can be monitored include amount and frequency of diarrhea excretion, quantitation of oocyst excretion, body weight, overall appearance and condition, blood chemistry and urine analysis of the infected individual's hepatobiliary function and culture of the parasite from body fluids and tissues.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

1. Feagin, J. E., Werner, E., Gardner, M. J., Williamson, D. H., and Wilson, R. J. (1992) *Nucleic Acids Res.* 20(4), 879–887
2. Gardner, M. J., Feagin, J. E., Moore, D. J., Rangachari, K., Williamson, D. H., and Wilson, R. J. M. (1993) *Nucleic Acids Res.* 21, 1067–1071
3. Gardner, M. J., Goldman, N., Barnett, P., Moore, P. W., Rangachari, K., Strath, M., Whyte, A, Williamson, D. H., and Wilson, R. J. (1994) *Mol. Biochem. Parasitol.* 66, 221–231
4. Divo, A. A., Geary, T. G., Jensen, J. B., and Ginsburg, H. (1985) *J. Protozool.* 32,442–446
5. Wilson, R. J. M., Denny, P. W., Preiser, P. R., Rangachari, K., Roberts, K., Roy, A., Whyte, A., Strath, M., Moore, D. J., Moore, P. W., and Williamson, D. H. (1996) *J. Mol. Biol.* 261, 155–172
6. McFadden, G. I., Reith, M. E., Munholland, J., and Lang-Umiasch, N. (1996) *Nature* 381, 482
7. Feagin, J. E., and Drew, M. E. (1995) *Exp. Parasitol.* 80, 430–440
8. Cundliffe, E. (1990) In: *The Ribosome, Structure, Function and Evolution*, Hill, W. E. Dahlberg, A. Garrett, R A. Moore, P. B. Schlessinger, D., and Warner, J. R. eds. American Society for Microbiology Press, Washington, D. C., pp.479–490
9. McCutchan, T. F., Li, J., McConkey, G. A, Rogers, M. J., and Waters, A. P. (1995) *Parasitol. Today* 11, 134–138
10. Waters, A. P., White, W., and McCutchan, T. F. (1995) *Mol. Biochem. Parasitol.* 72,227–237
11. Rogers, M. J., Gutell, R. R., Damberger, S. H., Li, J., McConkey, G. A., Waters, A P., and McCutchan, T. F. (1996) *RNA* 2, 134–145
12. Lu, M., and Draper, D. E. (1995) *Nucleic Acids Res.* 23, 3426–3433
13. Ryan, P. C., and Draper, D. E. (1991) *Proc. Natl. Acad Sci. U S. A.* 88, 6308–6312
14. Thompson, J., and Cundliffe, E. (1991) *Biochimie* 73, 1131–1135
15. Thompson, J., Musters, W., Cundliffe, E., and Dahlberg, A. E. (1993) *EMBO J.* 12, 1499–1504
16. Gutell, R. R, Gray, M. W., and Schnare, M. N. (1993) *Nucleic Acids Res.* 21, 3055–3074
17. Rosendahl, G., and Douthwaite, S. (1994) *Nucleic Acids Res.* 22, 357–363
18. Trager, W., and Jensen, J. B. (1976) *Science* 193, 673–675
19. Trager, W. (1994) *Methods Cell Biol.* 45, 7–26
20. McConkey, G. A, Ittarat, I., Meshnick, S. R.; and McCutchan, T. F. (1994) *Proc. Natl. Acad Sci. U S. A.* 91,4244–4248
21. Milhous, W. K, Weatherly, N. F., Bowdre, J. H., and Desjardins, R. E. (1985) *Antimicrob. Agents Chemother.* 27, 525–530
22. Geary, T. G., and Jensen, J. B. (1983) *Am J. Trop. Med Hyg.* 32,221–225
23. Li, J., Wirtz, R. A., McConkey, G. A, Sattabongkot, J., Waters, A. P., Rogers, M. J., and McCutchan, T. F. (1995) *Exp. Parasitol* 81, 182–190
24. Ranford-Cartwright, L. C., Balfe, P., Carter, R., and Walliker, D. (1991) *Mol. Biochem Parasitol.* 46, 185–187
25. Sambrook, J., Fritsch, E. F., and Maniatis, T. (1989) In: *Molecular Cloning; A Laboratory Manual*, 2nd Ed., Cold Sprig Harbor Laboratory Press, Cold Spring Harbor, N.Y.
26. Uchiuri, T., Wada, A., and Kominami, R. (1995) *J. Biol Chem.* 270,29889–29893.
27. Noller, H. F., Moazad, D., Stern, S., Powers, T., Allen, P. N., Robertson, J. M., Weiser, B., and Triman, K. (1990) In: *The Ribosome, Structure, Function and Evolution*, Hill, W. E. Dahlberg, A Garrett, R. A. Moore, P. B. Schlessinger, D., and Warner, J. R. eds., American Society for Microbiology Press, Washington, D. C., pp. 73–92
28. Divo, A. A., Geary, T. G., and Jensen, J. B. (1985) *Antimicrob. Agents Chemother.* 27, 21–27
29. Montandon, P. E., Nicolas, P., Schurmami, P., and Stutz, E. (1985) *Nucleic Acids Res.* 13,4299–4310
30. Fromm, H., Edelman, M., Aviv, D., and Galun, E. (1987) *EMBO J.* 6, 3233–3237
31. Gardner, M. J., Feagin, J. E., Moore, D. J, Spencer, D. F., Gray, M. W., Williamson, D. H., and Wilson, R. J. (1991) *Mol. Biochem. Parasitol* 48, 77–88
32. Strath, M., Scott-Finnigan, T., Gardner, M., Williamson, D., and Wilson, I. (1993) *Trans. R. Soc. Trop. Med Hyg.* 87, 211–216
33. Payne, D. (1987) *Parasitol Today* 3, 241–246
34. Clyde, D. F., Miller, R. M., DuPont, H. L., and Hornick, R. B. (1971) *J. Trop. Med. Hyg.* 74,238–241
35. Warrell, D. A (1993) In: *Bruce-Chwatt's EssentialMalanology*, Third Ed., Gilles, H. M., and Warrell, D. A, eds, Edward Arnold, London, pp. 176–177.
36. Martin, E. W. (ed.) Remington's Pharmaceutical Sciences, latest edition. Mack Publishing Co., Easton, Pa.
37. Strohl, W. R. & Floss, H. G. 1995. Thiopeptides. *Biotechnology* 28:223–238.
38. Blunt et al. (1997) *Clinical and Diagnostic Lab. Immunol.* 4:11–13.
39. Roberts, L. S. & Janovy, J., eds. *Foundations of Parasitology*, Fifth Edition, Wm. C. Brown, publishers.
40. Mankin, A. S., et al., 1994. Cross-hypersensitivity effects of mutations in 23 S rRNA yield insight into aminoacyl-tRNA binding.
41. Tzipori, S., et al., 1995. Evaluation of a two-phase scid mouse model preconditioned with anti-interferon-γ monoclonal antibody for drug testing against *Cryptoporidium parvum*. *J. Infect Dis.* 172:1160–1164.
42. Blagburn, B & Soave, ER. Prophylaxis and chemotherapy., pp. 112–115. In *Cryptospordium and cryptosporidiosis*, Fayer, R, ed. CRC Press.
43. Tzipori et al., 1994. *Clin Diagn. Lab. Immunol.* 1:450–456.
44. Walhiker et al., 1987. *Science* 236:1661–1666.
45. Arnon, R. (Ed.) *Synthetic Vaccines* 1:93–103, CRC Press, Inc., Boca Raton, Fla., 1987.

TABLE 1

| Drug | Conc. (μg/ml) | Parasite Count | Standard Deviation | Tox. O.D. | Standard Deviation | Inhibition Percent | Score | Toxicity Percent | Score |
|---|---|---|---|---|---|---|---|---|---|
| Media/DMSO | | 1037.56 | 176.02 | 1.100 | .346 | 00 | 0 | 00 | 0 |
| PRM/DMSO | 2000 μg/ml | 278.06 | 47.30 | .868 | .071 | 73.20 | 3 | 21.09 | 1 |
| Media-Infected | | NA | NA | .928 | .199 | NA | NA | 15.64 | 1 |
| Media-Lysed | | NA | NA | .852 | .051 | NA | NA | 22.55 | 1 |
| Thiostrepton | 100 μg/ml | 732.31 | 54.80 | .994 | .161 | 29.42 | 0 | 9.64 | 1 |
| | 10 | 909.25 | 128.71 | .991 | .134 | 12.37 | 0 | 9.95 | 1 |
| | 1 | 1193.19 | 57.34 | .941 | .350 | <0 | 0 | 14.50 | 1 |
| | .1 | 1052.13 | 104.48 | .912 | .029 | <0 | 0 | 17.14 | 1 |

Conc. - units = μg/ml; Parasite - Mean parasite count/field (16 fields at 10x mag. analyzed)

SD - Standard Deviation; % Inhib. - Percent inhibition of parasite infection

% Tox - Percent toxicity to cells by the drug; *NA - Not available due to toxicity Scores - expressed as range from 1 (non-toxic) to 4 (very toxic). Percent inhibition scores - expressed in ranges as 0: 0–30%; 1: 31–55%; 2: 56–70%; 3: 71–90%; and 4: 91–100%

TABLE 2

| Drug | Conc. (μg/ml) | Parasite Count | Standard Deviation | Tox. O.D. | Standard Deviation | Inhibition Percent | Score | Toxicity Percent | Score |
|---|---|---|---|---|---|---|---|---|---|
| Media/DMSO | | 1220.25 | 197.59 | 1.007 | .008 | .00 | 0 | .00 | 0 |
| PRM/DMSO | 2 mg/ml | 369.81 | 101.90 | .963 | .157 | 69.69 | 2 | 4.37 | 0 |
| Thiostrepton | 800 μg/ml | 149.25 | 27.49 | .676 | .049 | 87.77 | 3 | 32.87 | 2 |
| | 400 | 334.06 | 86.98 | .799 | .006 | 72.62 | 3 | 20.71 | 1 |
| | 200 | 587.81 | 140.82 | .820 | .185 | 51.83 | 1 | 18.62 | 1 |
| | 100 | 943.31 | 99.28 | .915 | .143 | 22.70 | 0 | 9.14 | 1 |
| Media | | 1811.69 | 376.93 | .914 | .010 | .00 | 0 | .00 | 0 |
| PRM | 2 mg/ml | 423.81 | 100.96 | .954 | .012 | 76.61 | 3 | −4.38 | 0 |

TABLE 3

Unwashed

| Drug | Conc. (μg/ml) | Parasite Count | Standard Deviation | Tox. O.D. | Standard Deviation | Inhibition Percent | Score | Toxicity Percent | Score |
|---|---|---|---|---|---|---|---|---|---|
| Media | | 1416.44 | 301.91 | 1.043 | .303 | .00 | 0 | .00 | 0 |
| Media/DMSO | | 1231.75 | 280.96 | 1.031 | .116 | .00 | 0 | 1.06 | 0 |
| Thiostrepton | 800 μg/ml | 106.06 | 45.04 | .739 | .231 | 91.39 | 4 | 29.11 | 2 |
| | 400 | 154.88 | 32.94 | .788 | .055 | 87.43 | 3 | 24.41 | 1 |
| | 200 | 391.19 | 107.54 | .827 | .122 | 68.24 | 2 | 20.67 | 1 |
| | 100 | 795.63 | 166.53 | .969 | .122 | 35.41 | 1 | 7.10 | 1 |
| PRM | 2000 | 256.38 | 64.76 | 1.061 | .290 | 81.90 | 3 | −1.73 | 0 |
| | 1000 | 293.56 | 96.74 | .963 | .097 | 79.27 | 3 | 7.67 | 1 |
| | 500 | 398.31 | 87.14 | 1.019 | .059 | 71.88 | 3 | 2.30 | 0 |
| | 250 | 453.94 | 74.96 | 1.121 | .165 | 67.95 | 2 | −7.53 | 0 |
| NTZ | 100 | NA | NA | .269 | .057 | NA | NA | 74.15 | 3 |
| | 10 | 87.31 | 20.74 | 1.302 | .338 | 92.91 | 4 | −24.94 | 0 |
| | 1 | 694.75 | 172.52 | .925 | .129 | 43.60 | 1 | 11.32 | 1 |
| | .1 | 1104.81 | 127.09 | .855 | .027 | 10.31 | 0 | 17.99 | 1 |
| Media-Inf | | NA | NA | .836 | .005 | NA | NA | 19.81 | 1 |
| Media-Lysate | | NA | NA | .859 | .040 | NA | NA | 17.55 | 1 |

TABLE 4

Washed at 4 hours

| Drug | Conc. (μg/ml) | Parasite Count | Standard Deviation | Tox. O.D. | Standard Deviation | Inhibition Percent | Score | Toxicity Percent | Score |
|---|---|---|---|---|---|---|---|---|---|
| Media | | 1210.28 | 209.00 | 1.041 | .116 | .00 | 0 | .00 | 0 |
| Media/DMSO | | 1395.69 | 184.63 | 1.033 | .303 | .00 | 0 | .77 | 0 |
| Thiostrepton | 800 | 176.31 | 25.36 | .739 | .231 | 87.37 | 3 | 29.01 | 2 |
| | 400 | 164.31 | 28.04 | .788 | .055 | 88.23 | 3 | 24.30 | 1 |

TABLE 4-continued

Washed at 4 hours

| Drug | Conc. (μg/ml) | Parasite Count | Standard Deviation | Tox. O.D. | Standard Deviation | Inhibition Percent | Score | Toxicity Percent | Score |
|---|---|---|---|---|---|---|---|---|---|
| | 200 | 297.19 | 52.99 | .827 | .122 | 78.71 | 3 | 20.56 | 1 |
| | 100 | 543.88 | 100.53 | .969 | .122 | 61.03 | 2 | 6.96 | 1 |
| PRM | 2000 | 211.38 | 70.20 | 1.061 | .290 | 82.54 | 3 | −1.87 | 0 |
| | 1000 | 251.88 | 83.69 | .963 | .097 | 79.19 | 3 | 7.54 | 1 |
| | 500 | 372.44 | 89.66 | 1.019 | .059 | 69.23 | 2 | 2.16 | 0 |
| | 250 | 492.13 | 226.63 | 1.121 | .165 | 59.34 | 2 | −7.68 | 0 |
| NTZ | 100 | NA | NA | .269 | .057 | NA | NA | 74.11 | 3 |
| | 10 | 96.06 | 35.55 | 1.302 | .338 | 93.12 | 4 | −25.12 | 0 |
| | 1 | 233.44 | 52.92 | .925 | .129 | 83.27 | 3 | 11.19 | 1 |
| | .1 | 1334.06 | 318.47 | .855 | .027 | 4.42 | 0 | 17.87 | 1 |
| Media-Inf | | NA | NA | .836 | .005 | NA | NA | 19.69 | 1 |
| Media-Lysate | | NA | NA | .859 | .040 | NA | NA | 17.44 | 1 |

TABLE 5

| Drug | | Conc. (μg/ml) | Parasite Count | Standard Deviation | Tox. O.D. | Standard Deviation | Inhibition Percent | Score | Toxicity Percent | Score |
|---|---|---|---|---|---|---|---|---|---|---|
| Media | | | 1273.06 | 209.80 | 1.148 | .078 | .00 | 0 | .00 | 0 |
| Media/DMSO | | | 960.19 | 178.72 | 1.015 | .129 | .00 | 0 | .00 | 0 |
| PRM | 0 hrs | 2000 μg/ml | 287.63 | 30.61 | .962 | .137 | 77.41 | 3 | 16.17 | 1 |
| | 2 hrs | 2000 | 134.94 | 32.98 | .878 | .058 | 89.40 | 3 | 23.49 | 1 |
| | 4 hrs | 2000 | 267.25 | 46.78 | .923 | .123 | 79.01 | 3 | 19.56 | 1 |
| | 8 hrs | 2000 | 354.06 | 71.53 | .871 | .176 | 72.19 | 3 | 24.05 | 1 |
| | 24 hrs | 2000 | 929.19 | 123.61 | .850 | .175 | 27.01 | 0 | 25.93 | 1 |
| Thiostrepton | 0 hrs | 800 | 112.44 | 23.10 | .783 | .002 | 91.17 | 4 | 22.91 | 1 |
| | 2 hrs | 800 | 104.19 | 30.87 | .577 | .136 | 91.82 | 4 | 43.15 | 2 |
| | 4 hrs | 800 | 196.81 | 73.44 | .638 | .085 | 84.54 | 3 | 37.14 | 2 |
| | 8 hrs | 800 | 192.56 | 35.92 | .786 | .048 | 84.87 | 3 | 22.56 | 1 |
| | 24 hrs | 800 | 318.25 | 42.22 | .749 | .138 | 75.00 | 3 | 26.26 | 2 |
| NTZ | 0 hrs | 10 | 113.06 | 24.44 | 1.236 | .120 | 91.12 | 4 | −21.72 | 0 |
| | 2 hrs | 10 | 53.94 | 13.71 | .900 | .032 | 95.76 | 4 | 11.38 | 1 |
| | 4 hrs | 10 | 112.31 | 37.04 | .952 | .108 | 91.18 | 4 | 6.16 | 1 |
| | 8 hrs | 10 | 178.13 | 42.78 | 1.014 | .008 | 86.01 | 3 | .10 | 0 |
| | 24 hrs | 10 | 501.63 | 139.70 | .990 | .005 | 60.60 | 2 | 2.41 | 0 |
| Media-Inf | | | NA | NA | .997 | .110 | NA | NA | 13.15 | 1 |
| Media-Lysate | | | NA | NA | 1.086 | .043 | NA | NA | 5.44 | 0 |

TABLE 6

| Drug | Conc. (μg/ml) | Parasite Count | Standard Deviation | Tox. O.D. | Standard Deviation | Inhibition Percent | Score | Toxicity Percent | Score |
|---|---|---|---|---|---|---|---|---|---|
| Media/DMSO | | 1372.19 | 16.00 | 1.647 | .001 | .00 | 0 | .00 | 0 |
| PRM/DMSO | 2 mg/ml | 325.75 | 87.10 | 1.273 | .112 | 76.26 | 3 | 22.74 | 1 |
| Thiostrepton | 800 μg/ml | 223.13 | 37.38 | .890 | .035 | 83.74 | 3 | 45.96 | 2 |
| | 400 | 288.13 | 53.38 | 1.146 | .124 | 79.00 | 3 | 30.45 | 2 |
| | 200 | 470.69 | 151.68 | 1.324 | .185 | 65.70 | 2 | 19.61 | 1 |
| | 100 | 871.25 | 139.37 | 1.348 | .242 | 36.51 | 1 | 18.15 | 1 |

TABLE 7

Oocyst shedding-last day of 10 day treatment

| Groups of 5 | Mean | +SD | % Inhib | Mucosal score | +SD |
|---|---|---|---|---|---|
| Group 1 (placebo) | 53.2 | 15.8 | — | 19.3 | 7.6 |
| Group 2 (2 × 250 mg/kg) | 11.2 | 5.1 | 78.9 | 9.8 | 5.3 |

What is claimed is:

1. A method for treating a parasitic infection in a subject infected with a parasite having a plastid-like organelle, comprising administering to the subject an infection treating amount of a thiopeptide in a pharmaceutically acceptable carrier, wherein the subject is a mammal.

2. The method of claim 1, wherein the mammal is a human.

3. The method of claim 1, wherein the parasite is from the Apicomplexa group of parasites.

4. The method of claim 3, wherein the parasite is selected from the group consisting of Plasmodium, Toxoplasma and Cryposporidium species.

5. The method of claim 4, wherein the parasite is Cryptospordium.

6. The method of claim 4, wherein the parasite is Toxoplasma.

7. The method of claim 4, wherein the parasite is Plasmodium.

8. The method of claim 1, wherein the thiopeptide is selected from the group consisting of thiostrepton, micrococcin, nosiheptide, siomycin, sporangiomycin, althiomycin, thiocilin and thiopeptin.

9. The method of claim 8, wherein the thiopeptide is thiostrepton.

10. The method of claim 1, wherein the thiopeptide is administered to the subject orally.

11. The method of claim 1, wherein the thiopeptide is administered to the subject parenterally.

12. A method for treating Cryptoporidium infection in a subject infected with a parasite having a plastid-like organelle comprising administering to the subject an infection treating amount of a thiopeptide in a pharmaceutically acceptable carrier, wherein the subject is a mammal.

13. The method of claim 12, wherein the mammal is a human.

14. The method of claim 12, wherein the thiopeptide is selected from the group consisting of thiostrepton, micrococcin, nosiheptide, siomycin, sporangiomycin, althiomycin, thiocillin and thiopeptin.

15. The method of claim 14, wherein the thiopeptide is thiostrepton.

16. The method of claim 12, wherein the thiopeptide is administered orally.

17. A method for treating a parasitic infection in a subject infected with a parasite having a plastid-like organelle, comprising administering to the subject an infection treating amount of a thiopeptide in a pharmaceutically acceptable carrier, wherein the parasitic infection is caused by a member of the Microspora phylum or Ascetospora phylum.

18. The method of claim 17, wherein the subject is a mammal.

19. The method of claim 18, wherein the mammal is a human.

20. The method of claim 17, wherein the thiopeptide is selected from the group consisting of thiostrepton, micrococcin, nosiheptide, siomycin, sporangiomycin, althiomycin, thiocillin, and thiopeptin.

21. A method for treating a subject infected with a parasite comprising administering a thiopeptide to the subject, wherein the parasite is selected from the group consisting of Plasmodium, Toxoplasma, and Cryptospordium.

22. The method of claim 21 wherein the parasite is Plasmodium.

23. The method of claim 21 wherein the parasite is Toxoplasma.

24. The method of claim 21 wherein the parasite is Cryptospordium.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 1:

GGGCTTTAGA AGCTTTTGG                                            19

(2) INFORMATION FOR SEQ ID NO: 2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 2:

CCATTTAAAA TTGGTAATCC TG                                        22

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 3:

GTGTGATAAT ATTCATGG                                             18

(2) INFORMATION FOR SEQ ID NO: 4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 4:

GGAGAGCATT TGGTG                                                15

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 5:

GTTTAGCTAT TAATATAGAA GC                                        22

(2) INFORMATION FOR SEQ ID NO: 6:

(i) SEQUENCE CHARACTERISTICS:
        (A) LENGTH: 18 base pairs
        (B) TYPE: nucleic acid

```
            (C) STRANDEDNESS: single
            (D) TOPOLOGY: linear (xi) SEQUENCE DESCRIPTION: SEQ ID NO: 6:

CGGAGAGGTA TTAATACC                                                    18

(2) INFORMATION FOR SEQ ID NO: 7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 7:

AAACTTGTGT TCGGATATAG                                                  20

(2) INFORMATION FOR SEQ ID NO: 8:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 8:

Ile Ala Ser Ala Ser Cys Thr Thr Cys Ile Cys Thr Cys Ser Cys
1               5                   10                  15

Ser Ser Ser
```